(12) United States Patent
Miyazaki (10) Patent No.: US 10,349,861 B2
(45) Date of Patent: Jul. 16, 2019

(54) GLASSES-SHAPED ELECTRONIC DEVICE

(71) Applicant: Alps Alpine Co., Ltd., Ota-ku, Tokyo (JP)

(72) Inventor: Shun Miyazaki, Miyagi-ken (JP)

(73) Assignee: Alps Alpine Co., Ltd., Tokyo (JP)

( * ) Notice: Subject to any disclaimer, the term of this patent is extended or adjusted under 35 U.S.C. 154(b) by 0 days.

(21) Appl. No.: 15/801,211

(22) Filed: Nov. 1, 2017

(65) Prior Publication Data

US 2018/0049664 A1 Feb. 22, 2018

Related U.S. Application Data

(63) Continuation of application No. PCT/JP2016/065827, filed on May 27, 2016.

(30) Foreign Application Priority Data

Jun. 1, 2015 (JP) ................................. 2015-111664

(51) Int. Cl.
*G02C 5/02* (2006.01)
*A61B 5/0496* (2006.01)
(Continued)

(52) U.S. Cl.
CPC ............ *A61B 5/0496* (2013.01); *A61B 3/113* (2013.01); *A61B 5/6803* (2013.01); *G02C 5/02* (2013.01);
(Continued)

(58) Field of Classification Search
CPC ... A61B 5/0496; A61B 5/6844; A61B 5/6803; A61B 3/113; A61B 3/10; A61B 5/0478;
(Continued)

(56) References Cited

U.S. PATENT DOCUMENTS 2,904,639 A * 9/1959 Mullin .................... G02C 11/06
351/178
2,916,538 A * 12/1959 Rose ....................... G02C 11/06
174/535
(Continued)

FOREIGN PATENT DOCUMENTS

JP H4-151620 5/1992
JP 2012-163640 8/2012
(Continued)

OTHER PUBLICATIONS

International Search Report from International Application No. PCT/JP2016/065827 dated Aug. 9, 2016.
(Continued)

*Primary Examiner* — William R Alexander
*Assistant Examiner* — Henry A Duong
(74) *Attorney, Agent, or Firm* — Beyer Law Group LLP (57) ABSTRACT

An FPC compartment in a left rim is slit-shaped. A left FPC positioning member supports a flexible printed circuit (FPC) in the FPC compartment such that a main surface of the FPC extends substantially horizontally. The FPC supported in the FPC compartment is twisted by substantially 90° at an entrance to a left hinge. The FPC extends around a hinge pin and is received in a left electronic-component compartment. The FPC is held in the left electronic-component compartment such that the main surface of the FPC extends substantially vertically. A left end piece located adjacent to the left hinge has a left cavity accommodating a left deformable bend of the FPC.

5 Claims, 10 Drawing Sheets (51) Int. Cl.
    G02C 5/14      (2006.01)
    A61B 3/113     (2006.01)
    A61B 5/00      (2006.01)
    G02C 5/22      (2006.01)
    G02C 11/00     (2006.01)
    A61B 5/0408    (2006.01)
    A61B 5/0478    (2006.01)
    A61B 5/11      (2006.01)

(52) U.S. Cl.
    CPC .............. *G02C 5/14* (2013.01); *G02C 5/22* (2013.01); *G02C 11/10* (2013.01); *A61B 5/0408* (2013.01); *A61B 5/0478* (2013.01); *A61B 5/11* (2013.01); *A61B 5/6844* (2013.01); *A61B 2562/0219* (2013.01)

(58) Field of Classification Search
    CPC ..... A61B 5/0408; A61B 3/102; A61B 3/1025; A61B 3/103; A61B 5/11; A61B 2562/0219; G02C 11/10; G02C 5/22; G02C 5/14; G02C 5/02; G02C 11/00
    USPC .......................................................... 351/205
    See application file for complete search history.

(56) References Cited

U.S. PATENT DOCUMENTS

| | | | | |
|---|---|---|---|---|
| 3,095,483 | A * | 6/1963 | Tresise | G02C 11/06 381/323 |
| 3,119,903 | A * | 1/1964 | Rosemond | G02C 11/06 351/140 |
| 5,606,743 | A * | 2/1997 | Vogt | H04B 1/086 16/228 |
| 5,835,185 | A | 11/1998 | Kallman et al. | |
| 6,769,767 | B2 * | 8/2004 | Swab | H04W 56/0015 351/158 |
| 7,527,374 | B2 | 5/2009 | Chou | |
| 8,801,174 | B2 | 8/2014 | Willey | |
| 8,994,612 | B2 | 3/2015 | Fujishiro | |
| 9,433,369 | B2 * | 9/2016 | Kanoh | A61B 3/10 |
| 2007/0200998 | A1 | 8/2007 | Schrimmer et al. | |
| 2015/0339511 | A1 | 11/2015 | Thomet et al. | |
| 2016/0026009 | A1 * | 1/2016 | Urbajs | G02C 7/101 349/13 |

FOREIGN PATENT DOCUMENTS

| | | |
|---|---|---|
| JP | 2013-244370 | 12/2013 |
| WO | 2013/175367 | 11/2013 |
| WO | 2013/188805 | 12/2013 |
| WO | 2014/048961 | 4/2014 |

OTHER PUBLICATIONS

European Search Report for European Application No. 16803288 dated Oct. 31, 2018.

* cited by examiner

GLASSES-SHAPED ELECTRONIC DEVICE

CLAIM OF PRIORITY

This application is a Continuation of International Application No. PCT/JP2016/065827 filed on May 27, 2016, which claims benefit of Japanese Patent Application No. 2015-111664 filed on Jun. 1, 2015. The entire contents of each application noted above are hereby incorporated by reference.

BACKGROUND OF THE INVENTION

1. Field of the Invention

The present invention relates to a glasses-shaped electronic device to be mounted on the head of a human to detect characteristics of the human.

2. Description of the Related Art

Electrodermal activity has been known as parameters indicating human psychological activity and physical conditions. For the electrodermal activity of a human, the potentials of the skin of the human are detected, so that the characteristics of the human can be detected.

Glasses-shaped electronic devices are currently required to detect the potentials of the skin of a human, particularly, the potentials (eye potentials) of the surface of the nose so that a variety of biological information about the human can be obtained based on the potentials. Examples of these devices include a device disclosed in Japanese Unexamined Patent Application Publication No. 2013-244370.

This device includes a pair of electrodes for detecting eye potentials such that the electrodes are arranged on the surfaces of nose pads of an eyeglass frame. The device further includes an electrode for detecting an eye potential such that the electrode is disposed on the surface of a bridge of the eyeglass frame.

The eye potentials detected by the electrodes are transmitted as electrooculogram signals to an external electrooculogram processing unit connected to the electrodes by electric wiring lines, serving as conductors. The processing unit processes the signals.

As regards how to route the electric wiring lines, the electric wiring lines can be arranged on the outside of the eyeglass frame. If the electric wiring lines are exposed on the outside of the eyeglass frame, a user may touch the electric wiring lines with, for example, his or her finger, when using the device. The electric wiring lines may be broken.

Although the electric wiring lines can be received in the eyeglass frame, it is difficult in view of structure to arrange the electric wiring lines in the eyeglass frame because the eyeglass frame is thin. A wiring operation is also complicated. When the electric wiring lines are arranged inside the eyeglass frame, it is necessary to maintain stable connection between electronic components included in the device.

SUMMARY OF THE INVENTION

The present invention has been made in view of such circumstances and provides a glasses-shaped electronic device having conductor wiring readily achieved in an eyeglass frame and capable of maintaining stable connection between electronic components included in the device without any possibility of a break in a conductor.

An aspect of the present invention provides a glasses-shaped electronic device including an eyeglass frame including a bridge, rims, hinges, and temples, and a flexible printed circuit having deformable bends. The eyeglass frame has a flexible printed circuit compartment extending through the bridge, the rims, the hinges, and the temples. The compartment accommodates the flexible printed circuit. The eyeglass frame has cavities arranged adjacent to the compartment in the hinges. The cavities accommodate the deformable bends of the flexible printed circuit. Such a configuration facilitates conductor wiring in the eyeglass frame and can maintain stable connection between electronic components included in the device without any possibility of a break in a conductor.

In this aspect, the flexible printed circuit compartment may be defined between two portions into which each of the bridge, the rims, the hinges, and the temples is divided. Such a configuration enables the flexible printed circuit to be readily received in the eyeglass frame.

In this aspect, the flexible printed circuit may be held in the compartment in the rims such that a main surface of the flexible printed circuit extends substantially horizontally. Preferably, parts of the flexible printed circuit extending from the deformable bends to the hinges are twisted by substantially 90° in the compartment adjacent to the hinges and the flexible printed circuit is held in the compartment in the temples such that the main surface extends substantially vertically. Preferably, parts of the flexible printed circuit adjacent to the bridge are twisted by substantially 90° in the compartment in the rims and the flexible printed circuit is held in the compartment in the bridge such that the main surface extends substantially vertically. Such a configuration allows the single flexible printed circuit to extend through the hinges, the rims, and the bridge without being exposed on the outside of the glasses-shaped electronic device. The glasses-shaped electronic device with excellent design quality can be provided.

In this aspect, the glasses-shaped electronic device may further include positioning members arranged in the compartment in the rims and mounted adjacent to the hinges. Preferably, the positioning members support the flexible printed circuit such that the main surface extends substantially horizontally. Such a configuration enables the flexible printed circuit to be received and positioned in the thin rims.

In this aspect, each of the positioning members may include a marker exposed at a front surface of the corresponding one of the rims. Such a configuration allows the markers to serve as references for measuring, for example, parallelism, to detect a performance characteristic, such as the posture, motion, or vibration of a user.

In this aspect, the glasses-shaped electronic device may further include a human characteristic detecting unit disposed in the bridge and configured to detect an eye potential while being in contact with a human nose. The flexible printed circuit may extend to right and left temple tips of the eyeglass frame such that the bridge of the eyeglass frame corresponds to middle part of the flexible printed circuit. The flexible printed circuit may be electrically connected to the human characteristic detecting unit in the bridge. Preferably, the flexible printed circuit is electrically connected at a first end to a battery disposed in one of the temple tips by a connector and is electrically connected at a second end to electric circuitry disposed in the other one of the temple tips by a connector. Such a configuration enables the electronic components included in the device to be connected by the single flexible printed circuit. The glasses-shaped electronic device including the electronic components connected by the single flexible printed circuit can be provided.

In this aspect, the glasses-shaped electronic device may further include positioning retainers arranged in the compartment. Preferably, the first and second ends of the flexible printed circuit in the compartment in the temples are attached to the connectors by the positioning retainers. Such a configuration can maintain stable attachment of the flexible printed circuit to the connectors.

DESCRIPTION OF THE PREFERRED EMBODIMENTS

Figure 1:
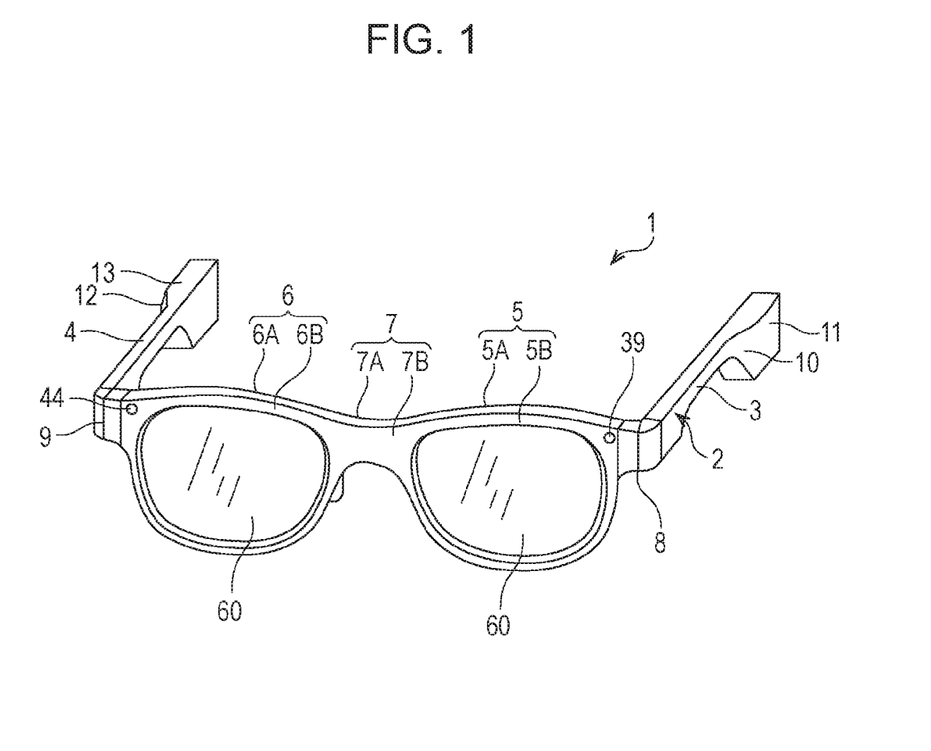
FIG. 1 is a front perspective view of a glasses-shaped electronic device according to an embodiment of the present invention.
Figure 2:
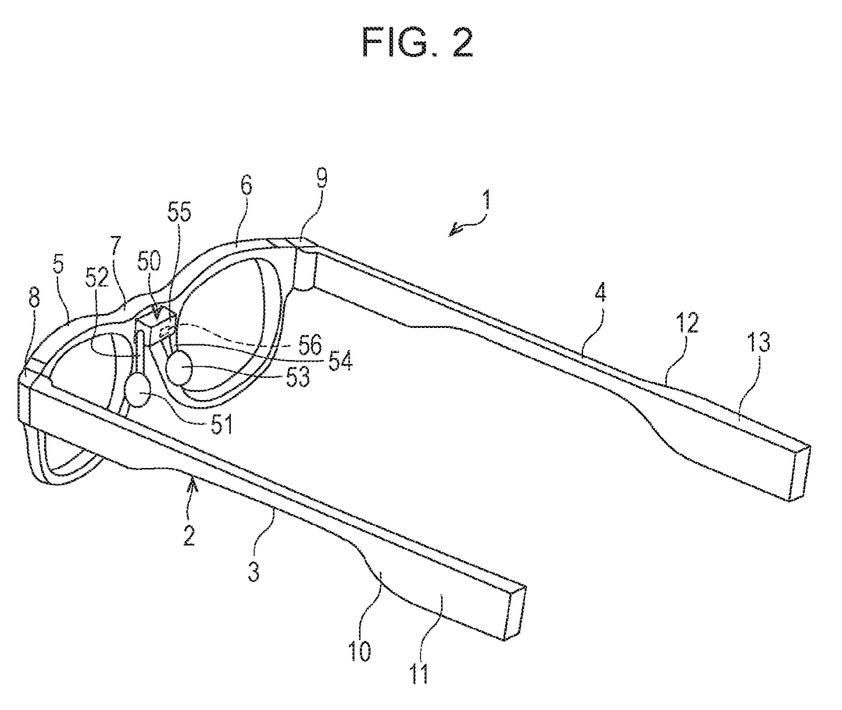
FIG. 2 is a rear perspective view of the glasses-shaped electronic device.

A glasses-shaped electronic device 1 according to an embodiment of the present invention will be described below with reference to the drawings. As illustrated in FIGS. 1 and 2, the glasses-shaped electronic device 1 includes an eyeglass frame 2 made of plastic.

The eyeglass frame 2 includes a left temple 3 to be put on the left ear of a human and a right temple 4 to be put on the right ear of the human. These temples 3 and 4, each of which is not angled for fitting on the ear, have a linear shape to hold right and left temporal portions of the head of the human. The eyeglass frame 2 including the temples 3 and 4 having such a shape provides a comfortable tight fit.

The eyeglass frame 2 further includes a left rim 5 and a right rim 6 to which lenses 60 are secured. The rims 5 and 6 are coupled by a bridge 7. Preferably, a human characteristic detecting unit 50, which will be described later, for detecting an eye potential is mounted in the bridge 7 such that the unit 50 can be placed on the nose of a human. The present invention can also be applied to a device that eliminates the human characteristic detecting unit 50.

In addition, a left hinge 8 is disposed between the left temple 3 and the left rim 5 and a right hinge 9 is disposed between the right temple 4 and the right rim 6. The temples 3 and 4 are connected to the rims 5 and 6 by the hinges 8 and 9, respectively, such that the temples are pivotable, or movable relative to the rims. When the glasses-shaped electronic device 1 is not used, typically, the left temple 3 of the eyeglass frame 2 is moved inwardly and the right temple 4 is then moved inwardly so as to be superposed on the left temple 3.

The left temple 3 is integrally formed with a left sloping portion 10 and a left temple tip 11, which serve as an end portion to be put on the left ear, such that the left sloping portion 10 is interposed between the left temple 3 and the left temple tip 11. The right temple 4 is integrally formed with a right sloping portion 12 and a right temple tip 13, which serve as an end portion to be put on the right ear, such that the right sloping portion 12 is interposed between the right temple 4 and the right temple tip 13. These temple tips 11 and 13 are typically called eyeglass tips, ear retainers, or ear pads. Part connecting the temple 3 and the temple tip 11 and part connecting the temple 4 and the temple tip 13 are portions on which the weight of the glasses-shaped electronic device 1 acts.

Figure 3:
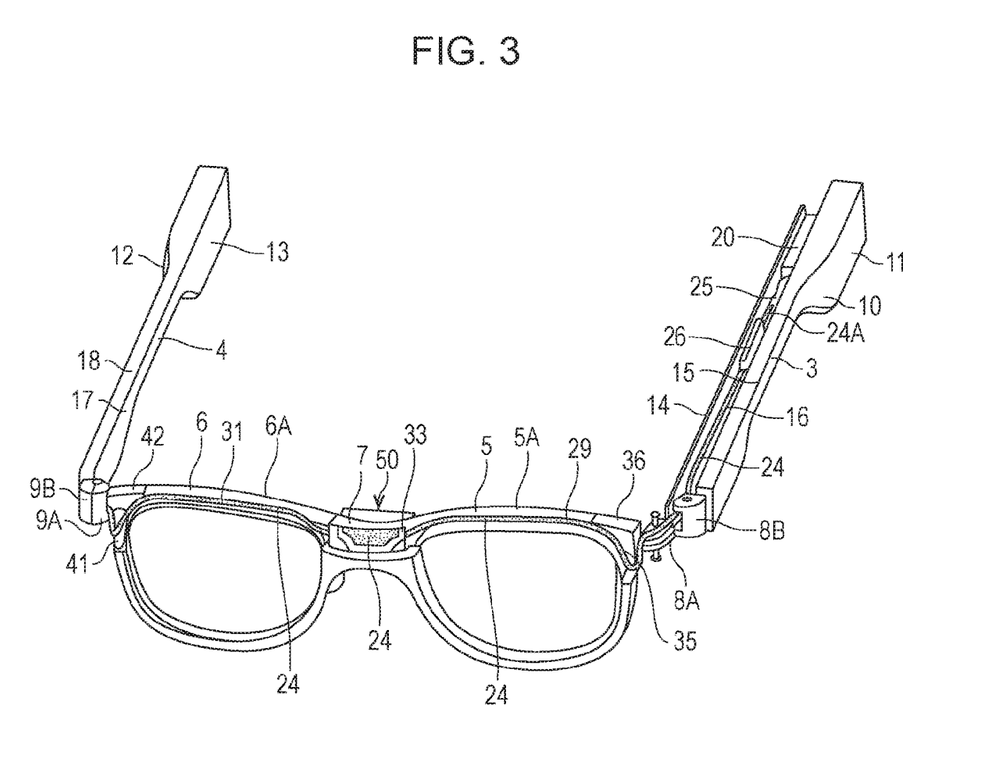
FIG. 3 is a partially cutaway perspective view of the glasses-shaped electronic device.

As illustrated in FIG. 3, the left temple 3 and the left temple tip 11 can be divided into two portions, or an inner half portion 14 and an outer half portion 15. The half portions 14 and 15 are superposed on each other to define therebetween an elongated left electronic-component compartment 16 extending through the left temple 3 and the left temple tip 11.

Figure 4:
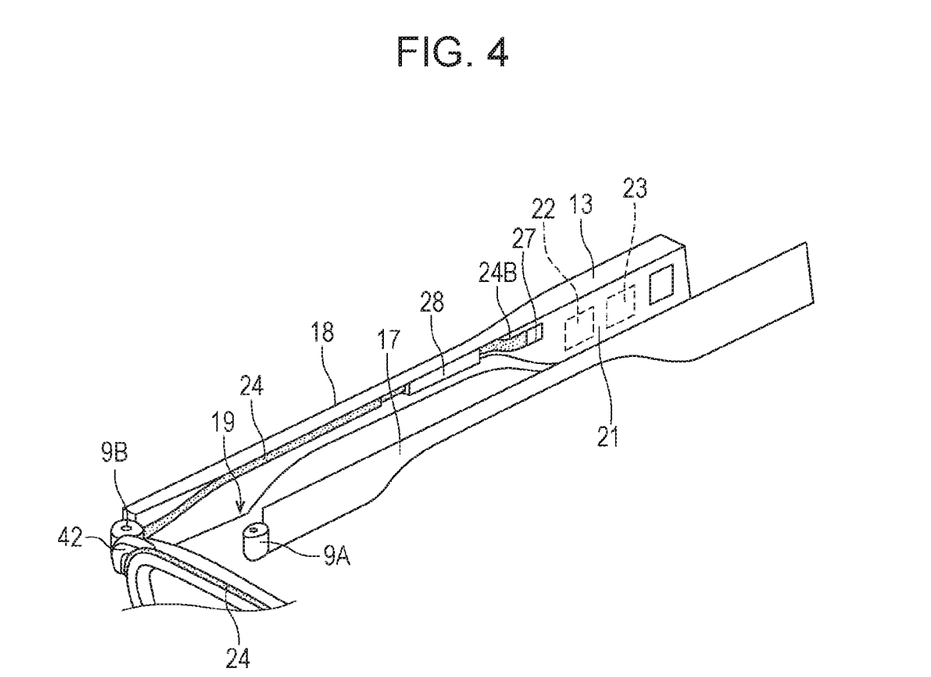
FIG. 4 is an exploded, enlarged perspective view of a right temple of the glasses-shaped electronic device.

As illustrated in FIG. 4, the right temple 4 and the right temple tip 13 can also be divided into two portions, or an inner half portion 17 and an outer half portion 18. The half portions 17 and 18 are superposed on each other to define therebetween an elongated right electronic-component compartment 19 extending through the right temple 4 and the right temple tip 13.

The sloping portions 10 and 12 allow the temple tips 11 and 13 to be thicker than the temples 3 and 4, respectively. Such a configuration provides larger storage spaces in the temple tips 11 and 13 than those in the temples 3 and 4.

The left electronic-component compartment 16 accommodates a rectangular battery 20 in the left temple tip 11. The battery 20 is mounted in the whole of the storage space, located in the left temple tip 11, in the left electronic-component compartment 16. The inside of the left temple tip 11 serves as a dedicated mounting space for the battery 20. Thus, a large capacity battery can be received.

The right electronic-component compartment 19 accommodates electric circuitry 21 in the right temple tip 13. The electric circuitry 21 includes a charging circuit 22 for the battery 20. A power switch unit (not illustrated) is disposed in the right temple tip 13.

The electric circuitry 21 includes electronic components, such as a sensor unit 23 for detecting the posture of a human. The sensor unit 23 includes an acceleration sensor and a gyroscopic sensor. The acceleration sensor is a sensor that detects acceleration acting on the glasses-shaped electronic device 1. The acceleration sensor detects angular velocities in a plurality of axial directions (e.g., two or three axes) orthogonal to each other or one another. The gyroscopic senor is a sensor that detects rotations acting on the glasses-shaped electronic device 1. The sensor unit in the present invention may include a six-axis gyroscopic sensor or a barometric pressure sensor. The sensor unit may include any kind of sensor.

The sensor unit 23 detects a performance characteristic of a user, for example, the posture, motion, or vibration of the user. A signal indicating the performance characteristic detected by the sensor unit 23 is transmitted to a portable communication terminal, such as a smartphone, by wireless communication, such as Bluetooth® or a wireless local area network (LAN).

The human characteristic detecting unit 50 is mounted in the bridge 7 of the eyeglass frame 2. The human characteristic detecting unit 50 detects the potential (e.g., eye potential) of the surface of the nose of a human. The detection can be used to obtain a variety of information, for example, information on fatigue of human eyes, based on the temperature of the skin.

The human characteristic detecting unit 50 includes a left nose electrode pad 51 that is to be located on a first side of the bridge of the nose of a human and is to contact the surface of the nose, a rod-shaped left nose electrode member 52 having an end to which the left nose electrode pad 51 is secured, a right nose electrode pad 53 that is to be located on a second side of the bridge of the nose of the human and is to contact the surface of the nose, and a rod-shaped right nose electrode member 54 having an end to which the right nose electrode pad 53 is secured.

The human characteristic detecting unit 50 further includes a plate-shaped glabella electrode pad 55 to contact the surface of part above the nose and between the eyebrows of a human and a rod-shaped glabella electrode member 56 having an end secured to central part of a rear surface of the glabella electrode pad 55.

The left nose electrode member 52, the right nose electrode member 54, and the glabella electrode member 56 are electrically connected to a printed wiring board 58 (refer to FIG. 9) disposed in the human characteristic detecting unit 50.

The left nose electrode member 52 detects the eye potential of the left eye, the right nose electrode member 54 detects the eye potential of the right eye, and the glabella electrode member 56 detects an eye potential. The present invention can also be applied to a device that eliminates the glabella electrode member 56.

Examples of a material for the left nose electrode member 52, the right nose electrode member 54, and the glabella electrode member 56 include copper, titanium, and stainless steel. The nose electrode members 52 and 54 and the glabella electrode member 56 may be made of a conductive material. For a material for the nose electrode pads 51 and 53 and the glabella electrode pad 55, each pad may be made of copper, titanium, or stainless steel. Each pad may be plated with, for example, copper or titanium.

The electronic-component compartments 16 and 19 accommodate a single flexible printed circuit (hereinafter, referred to as an FPC) 24. The FPC 24 establishes electrical connection between the battery 20, the electric circuitry 21, and the printed wiring board 58 in the human characteristic detecting unit 50. The use of the FPC 24 as conductor wiring lines in the glasses-shaped electronic device 1 facilitates wiring. In addition, since wiring lines of the FPC 24 are not exposed on the outside of the glasses-shaped electronic device 1, the glasses-shaped electronic device with excellent design quality can be provided.

The left electronic-component compartment 16 is defined between the two portions, or the inner half portion 14 and the outer half portion 15. The right electronic-component compartment 19 is also defined between the two portions, the inner half portion 17 and the outer half portion 18. To mount the FPC 24 in the electronic-component compartments 16 and 19, the inner and outer half portions 14 and 15 can be separated from each other and the inner and outer half portions 17 and 18 can be separated from each other. This leads to increased workability of mounting the FPC 24.

Figure 5:
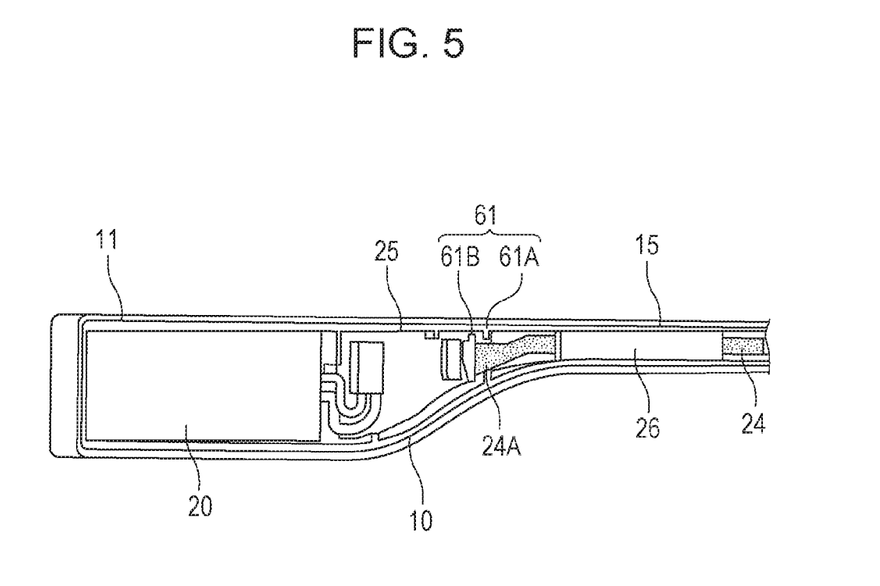
FIG. 5 is an exploded, enlarged perspective view of part including a left temple tip of the glasses-shaped electronic device.

As illustrated in FIG. 5, the left electronic-component compartment 16 accommodates a left connector 25 in the left sloping portion 10. Preferably, the battery 20 is connected to a left end 24A of the FPC 24 by the left connector 25.

Preferably, a left FPC positioning retainer 61 is disposed in the vicinity of the left connector 25 in the left electronic-component compartment 16. The left FPC positioning retainer 61 includes a rib 61A disposed in the outer half portion 15 and a flange 61B attached to the left end 24A of the FPC 24. Engagement of the flange 61B with the rib 61A prevents the left end 24A of the FPC 24 from detaching from the left connector 25. Thus, stable connection between the FPC 24 and the battery 20 can be maintained under tension on the FPC 24 when the FPC 24 is mounted in the left electronic-component compartment 16 or the left temple 3 is moved inwardly.

The left electronic-component compartment 16 further accommodates a left waterproof member 26 in the vicinity of the left connector 25. The left waterproof member 26 prevents, for example, moisture and dust, from entering the battery 20 and is made of, for example, PORON (registered trademark).

Figure 6:
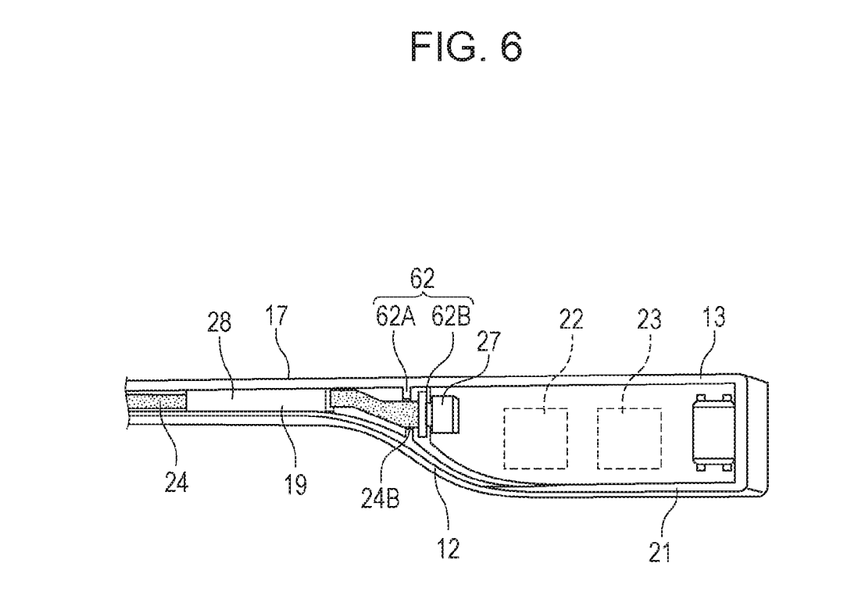
FIG. 6 is an exploded, enlarged perspective view of part including a right temple tip of the glasses-shaped electronic device.

As illustrated in FIG. 6, the right electronic-component compartment 19 accommodates a right connector 27 in the right sloping portion 12. Preferably, the electric circuitry 21 is connected to a right end 24B of the FPC 24 by the right connector 27.

Preferably, a right FPC positioning retainer 62 is disposed in the vicinity of the right connector 27 in the right electronic-component compartment 19. The right FPC positioning retainer 62 includes a rib 62A disposed in the outer half portion 17 and a flange 62B attached to the right end 24B of the FPC 24. Engagement of the flange 62B with the rib 62A prevents the right end 24B of the FPC 24 from detaching from the right connector 27. Thus, stable connection between the FPC 24 and the electric circuitry 21 can be maintained under tension on the FPC 24 when the FPC 24 is mounted in the right electronic-component compartment 19 or the right temple 4 is moved inwardly.

The right electronic-component compartment 19 further accommodates a right waterproof member 28 in the vicinity of the right connector 27. The right waterproof member 28 prevents, for example, moisture and dust, from entering the electric circuitry 21 and is made of, for example, PORON (registered trademark).

In the present invention, the FPC 24 may, instead of being a single piece, include a plurality of pieces coupled to each other or one another. The FPC has only to have a function of establishing electrical connection between the battery 20, the electric circuitry 21, and the printed wiring board 58 in the human characteristic detecting unit 50.

Figure 7:
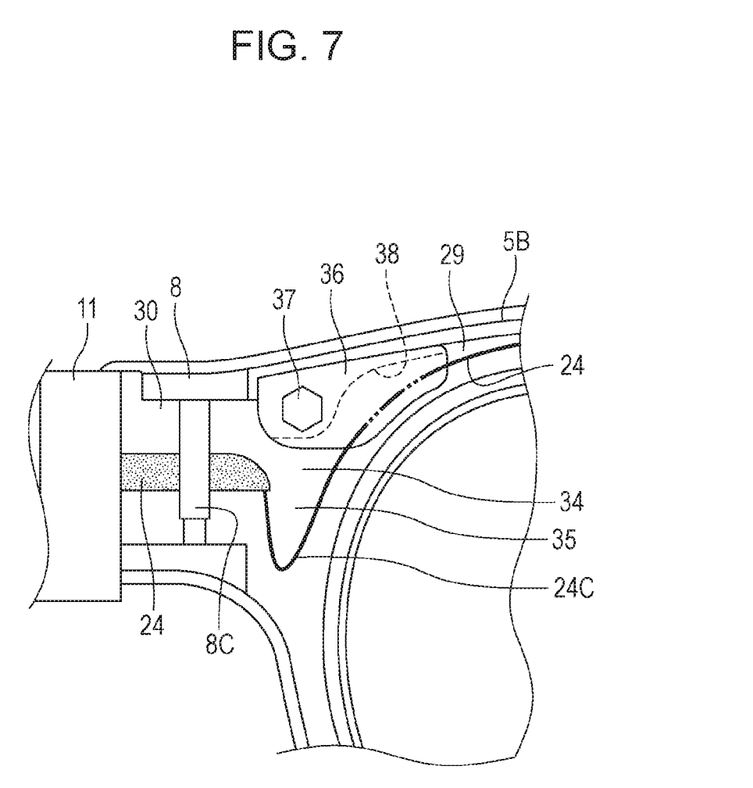
FIG. 7 is an exploded enlarged view of part including a left hinge of the glasses-shaped electronic device.

Upper part of the left rim 5 of the eyeglass frame 2 can be divided into two portions, or an inner half portion 5A and an outer half portion 5B. An FPC compartment 29 is defined between the half portions 5A and 5B. In addition, the left hinge 8 can also be divided into two portions, or an inner half portion 8A and an outer half portion 8B. As illustrated in FIG. 7, an FPC compartment 30 is defined between the half portions 8A and 8B. Thus, the left part of the FPC 24 is received such that the left part extends through the FPC compartment 29 in the left rim 5, the FPC compartment 30 in the left hinge 8, and the left electronic-component compartment 16.

Figure 8:
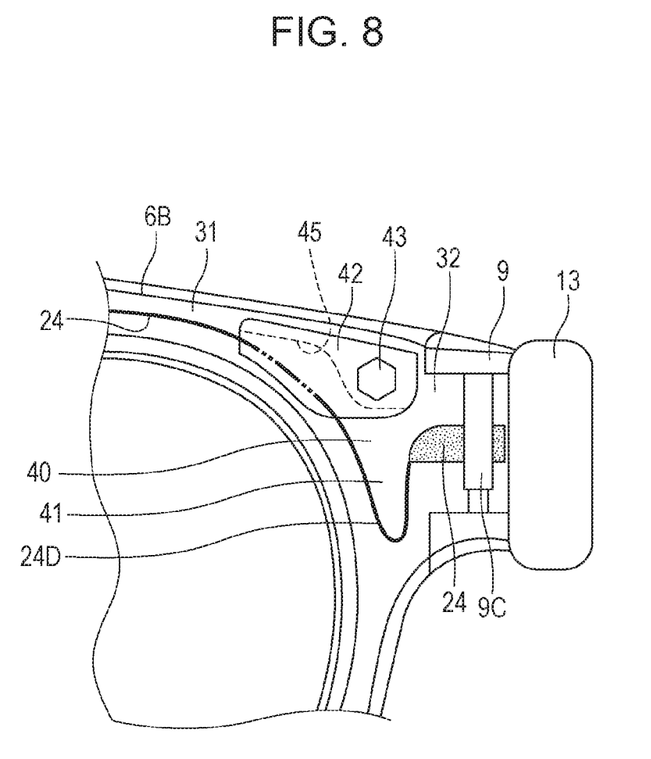
FIG. 8 is an exploded, enlarged perspective view of part including a right hinge of the glasses-shaped electronic device.

Upper part of the right rim 6 of the eyeglass frame 2 can also be divided into two portions, or an inner half portion 6A and an outer half portion 6B. An FPC compartment 31 is defined between the half portions 6A and 6B. In addition, the right hinge 9 can also be divided into two portions, or an inner half portion 9A and an outer half portion 9B. As illustrated in FIG. 8, an FPC compartment 32 is defined between the half portions 9A and 9B. Thus, the right part of the FPC 24 is received such that the right part extends through the FPC compartment 31 in the right rim 6, the FPC compartment 32 in the right hinge 9, and the right electronic-component compartment 19.

Figure 9:
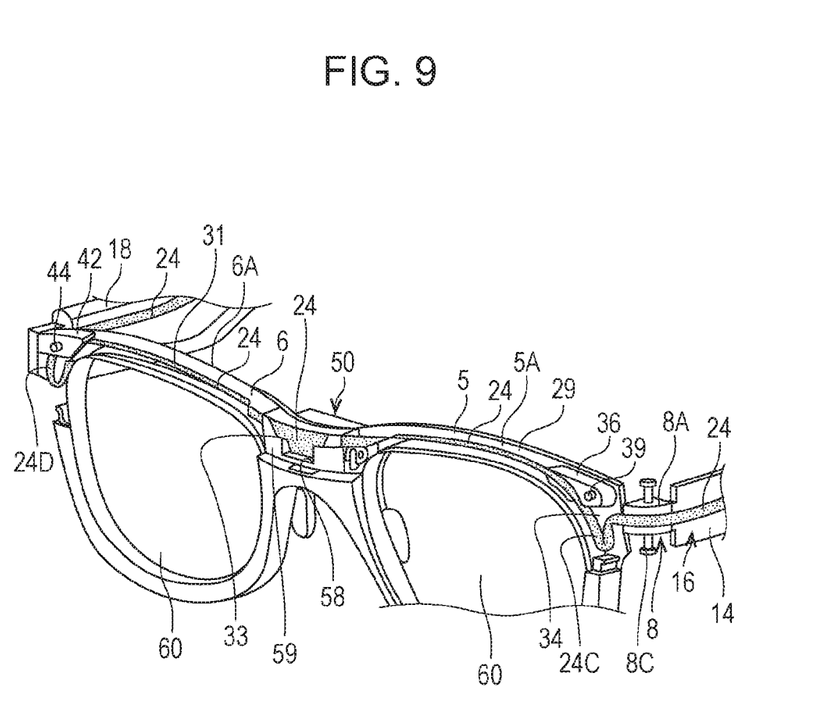
FIG. 9 is an exploded enlarged view of the glasses-shaped electronic device and illustrates a mounted state of a flexible printed circuit in the glasses-shaped electronic device.

The bridge 7 can also be divided into two portions, or an inner half portion 7A and an outer half portion 7B. As illustrated in FIG. 9, an FPC compartment 33 is defined between the half portions 7A and 7B. Thud, the left part and the right part of the FPC 24 join in the FPC compartment 33 in the bridge 7.

As illustrated in FIG. 7, the FPC compartment 29 in the left rim 5 is slit-shaped. In the FPC compartment 29, preferably, the FPC 24 is held such that a main surface of the FPC 24 extends substantially horizontally. Thus, the FPC 24 can be received in a narrow portion of glasses, such as a rim thereof.

The FPC 24 held in the FPC compartment 29 has a left deformable bend 24C. Preferably, part of the FPC 24 extending from the left deformable bend 24C to the left hinge 8 is twisted by substantially 90° at an entrance to the left hinge 8. The FPC 24 extends around a hinge pin 8C in the FPC compartment 30 and is received in the left electronic-component compartment 16. The FPC 24 is held in the left electronic-component compartment 16 such that the main surface of the FPC 24 extends substantially vertically.

A left end piece 34 is located adjacent to the left hinge 8. The left end piece 34 has a left cavity 35 accommodating the left deformable bend 24C of the FPC 24. Such a configuration prevents the FPC 24 from experiencing tension when the left temple 3 is moved inwardly, thus eliminating the possibility of a break in the FPC 24. The stable connection between the FPC 24 and the battery 20 can be maintained.

Preferably, a left FPC positioning member 36 for preventing the FPC 24 from floating in the FPC compartment 29 is secured by a pin 37 to the FPC compartment 29 in the left rim 5 such that the left FPC positioning member 36 is pressed against the outer half portion 5B of the left rim 5. The left FPC positioning member 36 supports the FPC 24 in the FPC compartment 29 such that the main surface of the FPC 24 can extend substantially horizontally if the FPC 24 is twisted in the left end piece 34, thus maintaining stable mounting of the FPC 24. The left FPC positioning member 36 has an FPC guide groove 38 having a function of guiding the FPC 24 in the FPC compartment 29. The FPC 24 is movable in the FPC guide groove 38.

When the FPC 24 is mounted in the left rim 5, the FPC 24 can be temporarily fixed in the FPC compartment 29 by the left FPC positioning member 36. The left rim 5 can be assembled without interference with the FPC 24.

The pin 37 is exposed at a front surface of the left rim 5. The exposed pin 37 may serve as a left marker 39 as a decorative member.

In the present embodiment, the FPC 24 is twisted and mounted. In the present invention, the FPC 24 may be received in the left rim 5 and the left temple 3 such that the FPC 24 extends from the left rim 5 to the left temple 3 without being twisted. In addition, the position of the left cavity 35 allowing deformation of the FPC 24 is not limited to the left end piece 34. The left cavity 35 has only to be disposed adjacent to the left hinge 8, provided that the left cavity 35 has a function of allowing deformation of the FPC 24.

As illustrated in FIG. 8, the FPC compartment 31 in the right rim 6 is slit-shaped. In the FPC compartment 31, preferably, the FPC 24 is held such that the main surface of the FPC 24 extends substantially horizontally. Thus, the FPC 24 can be received in a narrow portion of glasses, such as a rim thereof.

The FPC 24 held in the FPC compartment 31 has a right deformable bend 24D. Preferably, part of the FPC 24 extending from the right deformable bend 24D to the right hinge 9 is twisted by substantially 90° at an entrance to the right hinge 9. The FPC 24 extends around a hinge pin 9C in the FPC compartment 32 and is received in the right electronic-component compartment 19. The FPC 24 is held in the right electronic-component compartment 19 such that the main surface of the FPC 24 extends substantially vertically.

A right end piece 40 is located adjacent to the right hinge 9. The right end piece 40 has a right cavity 41 accommodating the right deformable bend 24D of the FPC 24. Such a configuration prevents the FPC 24 from experiencing tension when the right temple 4 is moved inwardly, thus eliminating the possibility of a break in the FPC 24. The stable connection between the FPC 24 and the electric circuitry 21 can be maintained.

Preferably, a right FPC positioning member 42 for preventing the FPC 24 from floating in the FPC compartment 31 is secured by a pin 43 to the FPC compartment 31 in the right rim 6 such that the right FPC positioning member 42 is pressed against the outer half portion 6B of the right rim 6. The right FPC positioning member 42 supports the FPC 24 in the FPC compartment 31 such that the main surface of the FPC 24 can extend substantially horizontally if the FPC 24 is twisted in the right end piece 40, thus maintaining stable mounting of the FPC 24. The right FPC positioning member 42 has an FPC guide groove 45 having a function of guiding the FPC 24 in the FPC compartment 31. The FPC 24 is movable in the FPC guide groove 45.

When the FPC 24 is mounted in the right rim 6, the FPC 24 can be temporarily fixed in the FPC compartment 31 by the right FPC positioning member 42. The right rim 6 can be assembled without interference with the FPC 24.

The pin 43 is exposed at a front surface of the right rim 6. The exposed pin may serve as a right marker 44 as a decorative member.

In the present embodiment, the FPC 24 is twisted and mounted. In the present invention, the FPC 24 may be received in the right rim 6 and the right temple 4 such that the FPC 24 extends from the right rim 6 to the right temple 4 without being twisted. In addition, the position of the right cavity 41 accommodating the right deformable bend 24D of the FPC 24 is not limited to the right end piece 40. The right cavity 41 has only to be disposed adjacent to the right hinge 9, provided that the right cavity 41 has a function of allowing deformation of the FPC 24.

Figure 10:
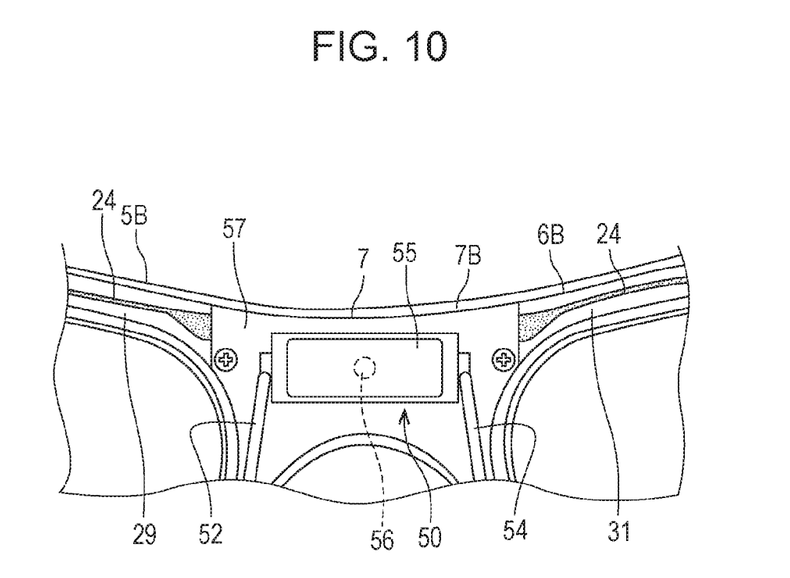
FIG. 10 is an exploded, enlarged, rear perspective view illustrating a bridge of the glasses-shaped electronic device.

As illustrated in FIG. 10, preferably, parts of the FPC 24 received in the FPC compartments 29 and 31 and located adjacent to the bridge 7 are twisted such that the main surface of the FPC 24 is turned by substantially 90°. The FPC 24 is caught by a central waterproof member 59, which is included in the human characteristic detecting unit 50 and is made of PORON (registered trademark), for example. The FPC 24 is attached to and pressed against an inner wall surface of the outer half portion 7B of the bridge 7 by a casing 57 of the human characteristic detecting unit 50 such that the main surface of the FPC 24 extends substantially vertically. Consequently, the FPC 24 is prevented from floating in the bridge 7, thus maintaining stable holding of the FPC 24.

Preferably, the FPC 24 in the human characteristic detecting unit 50 is electrically connected to the printed wiring board 58 such that a detection signal can be transmitted to the electric circuitry 21.

The left and right markers 39 and 44 are used as markers, serving as references for measuring, for example, parallelism, to detect a performance characteristic, such as the posture, motion, or vibration of the user.

The above-described glasses-shaped electronic device 1 enables the FPC 24 to establish electrical connection between the battery 20 disposed in the left temple tip 11 and the electric circuitry 21 disposed in the right temple tip 13. Such a configuration facilitates conductor wiring. In addition, this configuration eliminates the need for external arrangement of wiring lines. The glasses-shaped electronic device 1 with ease of use can be provided.

Since the FPC 24 can be received in the thin rims 5 and 6 and the temples 3 and 4, the glasses-shaped electronic device 1 with excellent design quality can be provided.

The arrangement of the cavities 35 and 41 accommodating the deformable bends 24C and 24D of the FPC 24 in the vicinities of the hinges 8 and 9 prevents the FPC 24 from experiencing unnecessary tension when the temples 3 and 4 are moved inwardly. This eliminates the possibility of a break in the FPC 24.

The FPC positioning retainers 61 and 62 prevent the respective ends 24A and 24B of the FPC 24 from detaching from the connectors 25 and 27. Thus, the stable connection between the FPC 24, the battery 20, the electric circuitry 21, and the human characteristic detecting unit 50 can be maintained.

The left temple tip 11 accommodates the battery 20 and the right temple tip 13 accommodates the electric circuitry 21. This arrangement allows the battery 20 to be separated from the charging circuit 22. In addition, the power switch unit is disposed adjacent to the electric circuitry 21. Such arrangement allows a reduction in the number of electric wiring lines of the FPC 24 adjacent to the battery 20, so that the electric wiring lines can be thickened.

The above-described embodiment is not intended to limit the present invention. It should be understood by those skilled in the art that various modifications, combinations, and alternations of the components of the above-described embodiment may be made within the technical scope of the present invention or the equivalents thereof.

The glasses-shaped electronic device according to the present invention is also used as a device to be mounted on the head of a human to detect the posture of the human, and can be used to collect data in order to, for example, prevent a driver of a car from dozing or increase the running speed of an athlete.

What is claimed is:

1. A glasses-shaped electronic device comprising:
an eyeglass frame having a bridge, a pair of rims, a pair of hinges, and a pair of temples; and
a flexible printed circuit having a pair of sagged bends,
wherein the eyeglass frame includes:
a compartment that accommodates the flexible printed circuit therein, the compartment extending on both sides from the bridge through the rims and the hinges to the temples; and
a pair of cavities that receive the pair of sagged bends from the compartment, the cavities being provided adjacent to the hinges,
wherein the flexible printed circuit includes a substrate having a main surface, the main surface extending substantially horizontally in the compartment in the rims, and extending substantially vertically in the compartment in the bridge and the temples,
wherein respective portions of the flexible printed circuit extending from the sagged bends to the hinges are twisted by substantially 90° in the compartment adjacent to the hinges such that the main surface becomes substantially vertical at the hinges,
and wherein respective portions of the flexible printed circuit adjacent to the bridge are twisted by substantially 90° in the compartment in the rims such that the main surface becomes substantially horizontal at the rims.

2. The electronic device according to claim 1, wherein each of the bridge, the rims, the hinges, and the temples is divided in half, the compartment being defined between respective two halves of the bridge, the rims, the hinges, and the temples.

3. The electronic device according to claim 1, further comprising:
positioning members disposed in the compartment in the rims adjacent to the respective hinges, the positioning members supporting the flexible printed circuit such that the main surface extends substantially horizontally.

4. The electronic device according to claim 3, wherein each of the positioning members includes a marker exposed at a front surface of the corresponding rims.

5. A glasses-shaped electronic device comprising:
an eyeglass frame having a bridge, a pair of rims, a pair of hinges, and a pair of temples; and
a flexible printed circuit having a pair of sagged bends,
wherein the eyeglass frame includes:
a compartment that accommodates the flexible printed circuit therein, the compartment extending on both sides from the bridge through the rims and the hinges to the temples;
a pair of cavities that receive the pair of sagged bends from the compartment, the cavities being provided adjacent to the hinges; and
first and second temple tips,
wherein the electronic device further comprises:
a human characteristic detecting unit disposed in the bridge and electrically connected to the flexible printed circuit in the bridge, the human characteristic detecting unit detecting an eye potential while being in contact with a human nose;
a battery disposed in the first temple tip and electrically connected to a first end of the flexible printed circuit by a first connector; and
electric circuitry disposed in the second temple tip and electrically connected to a second end of the flexible printed circuit by a second connector,
and wherein the flexible printed circuit extends from the bridge to the first and second temple tips such that the bridge of the eyeglass frame corresponds to a middle part of the flexible printed circuit and the first and second temple tips correspond to the first and second ends of the flexible printed circuit, respectively,
positioning retainers arranged in the compartment,
wherein the first and second ends of the flexible printed circuit in the compartment in the temples are attached to the first and second connectors, respectively, by the positioning retainers.

* * * * *